(12) United States Patent  
Edens et al.

(10) Patent No.: US 7,972,808 B2
(45) Date of Patent: Jul. 5, 2011

(54) PROTEIN HYDROLYSATE RICH IN TRIPEPTIDES

(75) Inventors: Luppo Edens, Rotterdam (NL); Petrus Jacobus Theodorus Dekker, Den Haag (NL); Andre Leonardus De Roos, Delft (NL)

(73) Assignee: DSM IP Assets B.V., Heerlen (NL)

( * ) Notice: Subject to any disclaimer, the term of this patent is extended or adjusted under 35 U.S.C. 154(b) by 293 days.

(21) Appl. No.: 12/039,973

(22) Filed: Feb. 29, 2008

(65) Prior Publication Data

US 2008/0220470 A1    Sep. 11, 2008

Related U.S. Application Data

(62) Division of application No. 10/516,983, filed as application No. PCT/EP03/05876 on Jun. 3, 2003, now abandoned.

(30) Foreign Application Priority Data

Jun. 4, 2002   (EP) .................................. 02100667

(51) Int. Cl.
*C12P 21/06* (2006.01)
*A61K 38/05* (2006.01)
*A61K 38/06* (2006.01)

(52) U.S. Cl. ................... 435/68.1; 424/94.63; 424/439; 514/17.2; 514/17.6; 514/17.7; 514/18.7; 514/21.9; 530/331

(58) Field of Classification Search .......................... None
See application file for complete search history.

(56) References Cited

U.S. PATENT DOCUMENTS

| | | | |
|---|---|---|---|
| 5,856,166 A | 1/1999 | Bartfeld et al. | |
| 5,856,308 A | 1/1999 | St. Pierre et al. | |
| 6,310,041 B1 | 10/2001 | Haddox et al. | |
| 2005/0256057 A1 | 11/2005 | Edens et al. | |

FOREIGN PATENT DOCUMENTS

| | | |
|---|---|---|
| EP | 0 321 603 | 6/1989 |
| EP | 0 325 986 | 8/1989 |
| EP | 0 522 428 | 1/1993 |
| EP | 0 967 285 | 12/1999 |
| JP | 02-039896 | 2/1990 |
| JP | 05-015314 | 1/1993 |
| JP | 08-308565 | 11/1996 |
| WO | WO-95/17512 | 6/1995 |
| WO | WO-96/13174 | 5/1996 |
| WO | WO-96/14404 | 5/1996 |
| WO | WO-97/00078 | 1/1997 |
| WO | WO-98/51803 | 11/1998 |
| WO | WO-99/02705 | 1/1999 |
| WO | WO-99/16461 | 4/1999 |
| WO | WO-00/52147 | 9/2000 |
| WO | WO-01/32905 | 5/2001 |
| WO | WO-01/68114 | 9/2001 |
| WO | WO-02/45524 | 6/2002 |
| WO | WO-02/68623 | 9/2002 |

OTHER PUBLICATIONS

Ito et al, "A tripeptides 'anticodon' deciphers stop codons in messenger RNA", Nature 403, pp. 680-684 (Feb. 10, 2004).
Pfister et al, Abstract "Identification and Synthesis of Chemotactic Tripeptides from Alkali-degraded Cornea a study of N-acetyl-Proline-Glycine-Proline and N-methyl-Proline-Glycine-Proline", Investigative Ophthalmology and Visual Science, Jun. 1995; 36(7):1306-16.
Ashmarin et al., Biochemistry (Moscow) (1998) 63(2):119-124.
Bernejo and Polanco, Rev. Neurol. (2002) 34(Suppl. 1):S24-S33.
Diefenthal and Dargatz, World Journal of Microbiology & Biotechnology (1995) 11:209-212.
Doring et al., J. Biol. Chem. (1998) 273:23211-23218.
Grimble, Annu. Rev. Nutr. (1994) 14:419-447.
International Search Report for PCT/EP03/05876, mailed on Aug. 21, 2003, 3 pages.
Kanatani et al., J. Biochem. (1993) 113:790-796.
Nielsen et al., Journal of Food Science (2001) 66(5):642-646.
Pihlanto-Leppala, Trends in Food Science & Technology (2001) 11:347-356.
Shan et al., Science (2002) 297:2275-2279.
Carter et al "A novel role for proline in plant floral nectars" Naturwissenschaften (2006) 93: 72-79.

*Primary Examiner* — Herbert J. Lilling
(74) *Attorney, Agent, or Firm* — Nixon & Vanderhye P.C.

(57) ABSTRACT

The present invention describes a protein hydrolysate which is rich in tripeptides whereby the tripeptides are rich in proline at one end of the peptide.

6 Claims, 3 Drawing Sheets

PROTEIN HYDROLYSATE RICH IN TRIPEPTIDES

Figure 1:
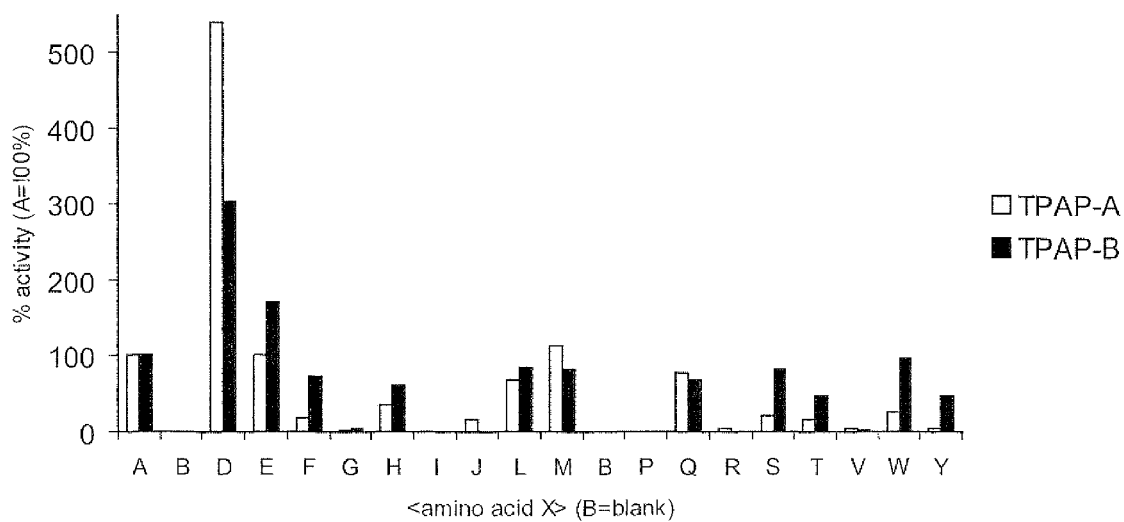
Figure 2B:
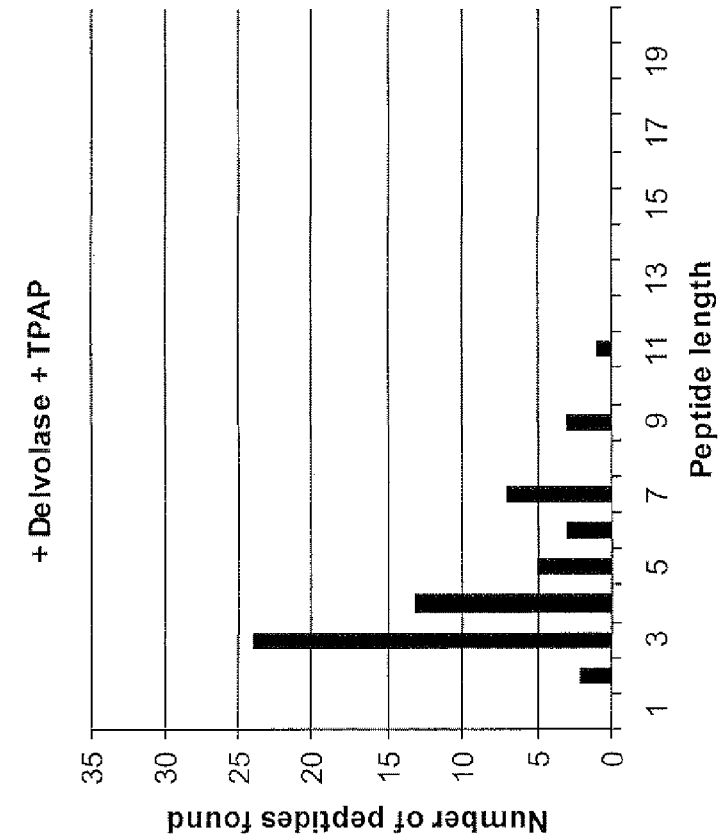
Figure 2A:
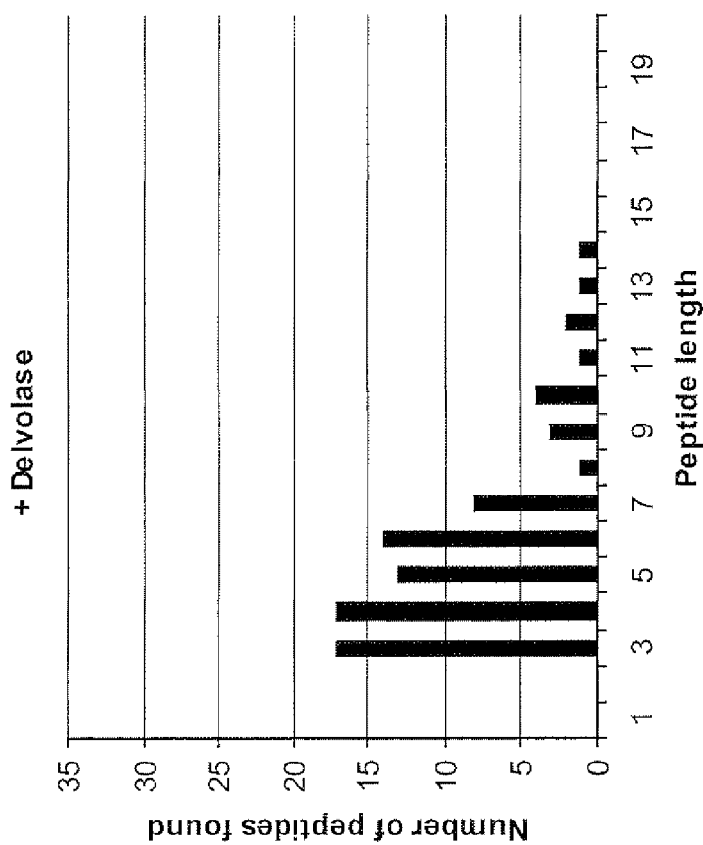
Figure 2D:
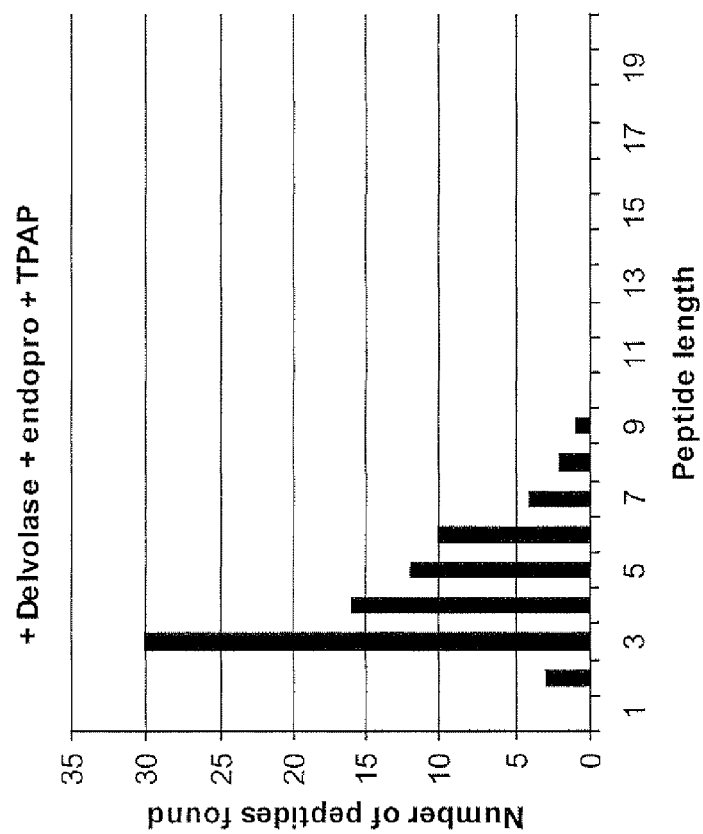
Figure 2C:
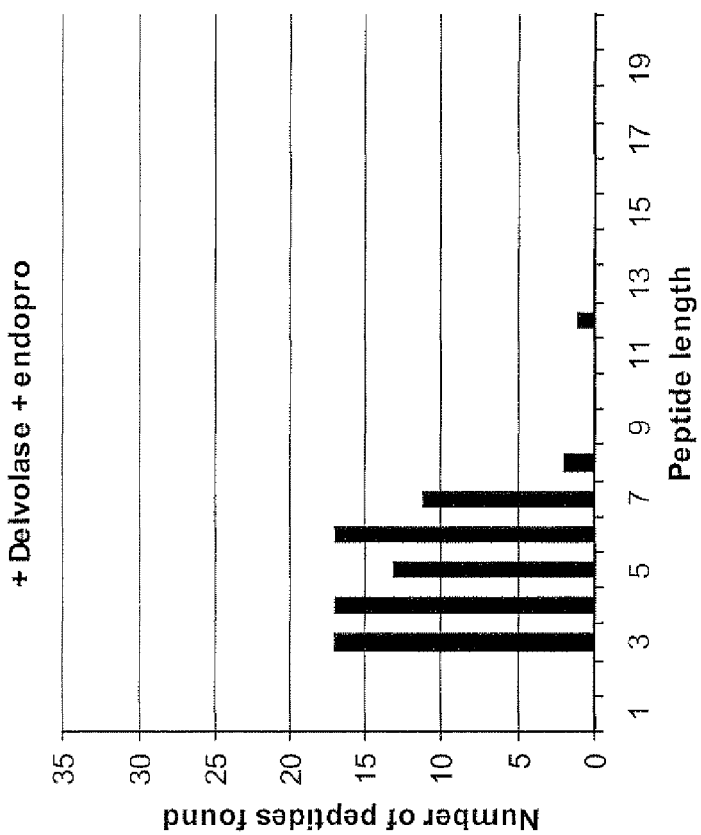

This application is a divisional of application Ser. No. 10/516,983, filed Dec. 3, 2004 (abandoned), which is a U.S. national phase of international application PCT/EP03/05876, filed Jun. 3, 2003, which designated the U.S. and claims benefit of EP 02100667.1, filed Jun. 4, 2002, the entire contents of each of which are hereby incorporated by reference in this application.

FIELD OF THE INVENTION

The present invention relates to protein hydrolysate and the uses thereof.

BACKGROUND OF THE INVENTION

There is increasing interest in the use of protein hydrolysates for both medical and non-medical applications. In both applications an easily assimilable diet featuring facilitated gastrointestinal uptake of proteins is a factor of prime importance. Protein hydrolysates for medical applications also require strongly reduced allergenic properties. For products intended for non-medical applications, good taste characteristics and good solubilities under acid conditions are important characteristics. Unfortunately the hydrolysis process required to realise these benefits comes with a number of disadvantages. These include bitter off-tastes, residual immunogenic materials, low yields of nutritionally indispensible amino acids, high osmotic values caused by the release of free amino acids and, finally, limited acid stabilities.

In prior publications several enzyme mixtures aimed at optimising hydrolysate characteristics and lowering production costs have been described. All of these publications refer to the use of single or mixed endoproteases. Examples include EP 321 603, which refers to the use of animal-derived endoproteases like trypsin, chymotrypsin and pancreatin, and EP 325 986 and WO 96/13174, which favor the use of endoproteases obtained from *Bacillus* or *Aspergillus* species. Unfortunately these enzyme combinations always yield peptide mixtures which are bitter and exhibit a broad molecular weight distribution. Large molecular weight peptides are undesirable because they are responsible for the allergenic response and their uptake requires additional enzymatic processing steps in the intestine. Reducing the bitter off-taste in the hydrolysates makes the use of exoproteases such as aminopeptidases or carboxypeptidases indispensible. Disadvantages of this debittering process are the release of substantial quantities of free amino acids and thus brothy off flavors and losses of nutritionally important amino acids.

In conclusion, industrial production of protein hydrolysates continues to rely on enzyme mixtures which are far from optimal so that expensive purification steps are needed to produce peptide mixtures having sub-optimal size distributions.

Upon normal dietary intake the proteins present in food are gradually hydrolysed to smaller fragments which are finally transported across the wall of the small intestine. During passage through the gastrointestinal tract a number of different proteases that originate in the stomach, pancreas and small intestine are active. Endoproteases such as pepsin, trypsin and chymotrypsin cleave the large molecular weight proteins into smaller oligopeptides. These oligopeptides are then further hydrolysed by a number of other enzymes such as di- and tripeptidyl peptidases as well as amino- and carboxypeptidases. The final steps of hydrolysis take place in the small intestine and result in a mixture of free amino acids and di- and tripeptides (Grimble, G. K. 1994. Annu. Rev. Nutr. 14; 419-447).

Despite the large collection of proteases that is active in the gastrointestinal tract, it is likely that peptides that resist further proteolytic hydrolysis in the small intestine form a major fraction of the surviving population of di- and tripeptides. It has, for example, been reported that di- and tripeptides carrying carboxyterminal proline residues exhibit stabilities in the body which are up to 3 orders of magnitude higher than other peptides (Ashmarin, I. P. et al.; Biochemistry (Moscow), Vol 63, No 2, 1998, pp 119-124). Carrier systems specific for the transport of either the free amino acids or the di- and tripeptides are responsible for the efficient transport across the intestine wall. A peptide sequence-independent mechanism capable of transporting quantitatively significant amounts of intact di- and tripeptides has been identified (Doering, F. et al; 1998; J. Biol. Chem. 273, 23211-23218). After entering the blood circulation, the peptides may potentially act as physiological modulators of metabolism. The physiological effects of peptides with opioid, ACE-inhibitory, antithrombosis, antiulcer, antiarthritic and anorectic activities have been described (Pihlanto-Leppala, A; Trends in Food Science & Technology 11 (2001) 347-356; Ashmarin, I. P. et al.; Biochemistry (Moscow), Vol 63, No 2, 1998, pp 119-124).

The recent commercialisation of various protein hydrolysates claiming antihypertensive effects emphasize the increased scope of use of protein hydrolysates containing "bioactive" peptides in medical and non-medical applications. These bioactive peptides and protein hydrolysates containing such bioactive peptides have been described in a number of patent applications. For example, WO 97/00078 describes hydrolysates obtained by incubation with probiotic bacteria or enzymes obtained from such bacteria. WO 99/16461 describes the inhibition of angiotensin-converting enzyme by specific tripeptides obtained by fermentation of Lactobacillus. WO 01/32905 describes the preparation of a product containing antihypertensive peptides by fermenting casein with lactic acid bacteria. Several other applications (see for example WO 01/68114) describe the use of highly purified or chemically synthesized peptides for reducing blood pressure or treating diabetes, renal impairment or obesity.

DESCRIPTION OF THE INVENTION

The present invention provides a process to produce protein hydrolysate which is rich in tripeptides whereby the peptides preferably are rich in proline at one end of the peptide and preferably the peptide has a carboxy terminal proline. Preferably the protein hydrolysate of the invention is non-bitter. The hydrolysate may optionally comprise dipeptides.

According to a preferred embodiment of the process of the invention, the selected protein or proteinaceous substrate is contacted with a suitable endoprotease. This suitable endoprotease is preferably a proline specific endoprotease (PSE or Endopro), a serine protease, a metalloendoprotease or an aspartic protease, more preferably a PSE is used. Moreover this substrate is contacted with a suitable tripeptidase (TPAP) or a mixture of tripeptidases. Such tripeptidases are defined as enzymes capable of releasing tripeptides from a polypeptide, either from the N-terminal side of the polypeptide hereby encompassing the socalled tripeptidyl-peptidases or from the C-terminal side of the polypeptide hereby encompassing the socalled peptidyl-tripeptidases. Advantageously the protein substrate is first fermented with a endoprotease, such as a serine protease, metalloendoprotease or an aspartic protease, to partly hydrolyse the protein. We have found that the TPAP is, in general, more effective on such prehydrolysed protein substrates.

The process according to the invention involves a combination of one or more endoproteases with one or more tripeptidases. Advantageously the enzymes are used in an isolated form and in an endoprotease to tripeptidase protein ratio range between 1:0.05 and 1:50, preferably between 1:0.1 to 1:10.

The protein substrate or the partial hydrolysate formed can first be subjected to the suitable first endoprotease and subsequently the TPAP or mixture of TPAP's can be added. In cases where the optimal activity conditions of the enzymes are roughly identical, a one step process may be preferred. Preferably the TPAP used in the present process, is a TPAP which after an incubation at pH5 of 1 hour at 50° C. shows at least 70% residual activity on a Ala-Ala-X-pNa substrate as measured in Example 1, X may vary with the TPAP in question depending on the specificity of the TPAP. X is an amino acid residue which gives rise to at least an significant activity of the TPAP (see for example FIG. 1.)

To be useful as processing aids in the preparation of food ingredients, an enzyme must preferably meet a number of strict economical and legislative criteria. To meet the legislative criteria the enzyme should be obtained from an unsuspect source, for example a food-grade microorganism. To meet the economical criteria, the enzyme should be secreted by the microorganism, producible in high yields and exhibit a number of biochemical characteristics such as a long term stability under industrial processing conditions. To minimise the risks of microbial infections under such non-sterile conditions, industrial processing often employs acidic pH conditions and a temperature of 50 degrees C. or higher. An enzyme used in the present invention advantageously meet these demands.

The present invention further provides a hydrolysate rich in tripeptides whereby preferably these tripeptides are rich in carboxy terminal proline. Rich in tripeptides means that at least 20 molar %, preferably at least 25 molar %, more preferably at least 30 molar % or most preferably at least 35 molar % of the smaller peptides present in the hydrolysate, is present as tripeptide. Smaller peptides are defined as peptides with a molecular weight of 200-2000 Da. Rich in proline means that at least 20%, preferably at least 30%, more preferably at least 40% and even more preferably 50% of the proline present in the starting protein substrate, is present in the tripeptides, preferably as carboxy terminal proline. Preferably 30% of the tripeptides or more preferably 35% of the tripeptides have a carboxy terminal proline residue, the values can be obtained with protein substrates that are rich in proline.

The hydrolysate produced according to the present invention has in general a degree of hydrolysis of between 10 and 40, preferably between 15 and 30. The degree of hydrolysis is determined using the OPA method as described by Nielsen, P. M. et al (Journal of Food Science, Vol 66, No 5, PP 642-646, 2001). The hydrolysates produced according to the process of the present invention can be fractionated if desired. For example separation techniques such as centrifugation or filtration (for example microfiltration and ultrafiltration) can be used to produce compositions which are further enriched in peptides having a molecular weight of 2000 Da or less. In this way it is possible to produce a composition comprising for at least 10 wt %, preferably for at least 20 wt %, more preferably for at least 30% and most preferably for at least 40 wt % of peptides having a molecular weight of 200-2000 Da, based on total amount of peptides present.

Although the main products containing protein hydrolysates are infant formula and food products for hospitalised persons, products intended for persons with non-medical needs, such as athletes or people on a slimming diet, are becoming more common.

Whey protein represents a very suitable substrate for producing hydrolysates by the process of the invention. Whey protein is relatively rich in "essential" and "branched chain" amino acids and has a high biological digestibility. Moreover, whey hydrolysates exhibit relatively low bitterness profile. Because whey has a relatively low proline content, the role of the tripeptidase in generating a mixture of easily assimilable peptides is important.

In comparison with whey, proteins like casein, wheat and maize gluten, soy, rice protein, chicken feathers and gelatin exhibit vastly different amino acid compositions. On the basis of their amino acid composition, some of these proteins potentially form the substrate of choice for the production of hydrolysates by the process of the invention. For example, wheat gluten is extremely rich in glutamine and rice protein is rich in arginine residues. Both amino acids are known to improve physical endurance and the recovery rate following high intensity exercise. However, as a free amino acid, glutamine is not stable so that supply in a readily assimilable peptide is advantageous. Maize gluten is a cheap substrate that is extremely rich in leucine and phenylalanine, it is known that these amino acids can modulate glucose and insulin responses upon oral consumption. Chicken feathers as well as whey protein form a cheap and potentially important source of cysteine, an amino acid with an important role in modulating immune functions and fighting oxidative stress. Like glutamine, cysteine is a labile compound that is preferably supplied in the form of di- or tripeptides. However, up to the present invention the development of optimized hydrolysis protocols for such products were economically not viable.

Casein, gelatin and wheat and maize gluten all contain high levels of proline residues i.e. more than 6 grams free amino acid per 100 grams of protein. As mentioned before, proline confers an increased stability to peptides thereby increasing their potential significance in eliciting physiological effects such as decreasing blood pressure, acting as opioid agonists or antagonists, contracting smooth muscles and inhibiting platelet aggregation. Moreover, recent research has implicated specific proline containing sequences or a shortage of proline-specific proteases to immunological effects associated with psychological features. For example celiac sprue is a widely prevalent autoimmune disease induced by exposure to dietary gluten (Shan, L. et al; Science Vol 297, 2002, 2275-2279) and linked with behaviour change (Bernejo, M. and Polanco I, Rev Neurol 2002 Feb. 28; 34 Suppl 1: S24-33).

Up to now peptide bonds involving proline residues have been notoriously difficult to cleave using commercially available enzymes so that protein hydrolysates prepared from proline-rich substrates contain major fractions of large molecular weight material. Moreover, proline represents a very hydrophobic amino acid and yields extremely bitter hydrolysates. Thus, the production of acceptable hydrolysates from proline-rich substrates using existing technologies would lead to low yields and highly priced products.

Most commercially available endoproteases exhibit a strong preference for cleaving at the carboxyterminal side of either hydrophobic amino acid residues such as Phe, Tyr or Leu or at the carboxyterminal side of basic residues like Lys and Arg. In order to make a hydrolysate that is relatively rich in small peptides, the above mentioned proline-specific protease is undoubtedly an important addition to the tool box. However, many proteins have a surprisingly high content of glutamine/glutamate and asparagine/aspartate residues so that a tripeptidase able to cleave behind these residues can be highly advantageous.

Against this background protein hydrolysates rich in di- and tripeptides present the ideal products for facilitated gastrointestinal uptake. Currently protein hydrolysates are made using industrially available endoproteases so that the formation of di- and tripeptides in such products is random and far from optimal. Although di- and tripeptidylpeptidases are known, most of these enzymes were obtained from mammalian sources so that these enzymes are not suitable for industrial application. The few enzymes described for microbial sources are either cytosolic, i.e. they are not secreted or display unfavorable pH and temperature optima (Springer Handbook of Enzymes, Volume 6, Class 3.4; Second Edition, ISBN 3-540-43012-1; and WO 96/14404).

Hitherto cost-effective, potentially food-grade tripeptidases that could be used under industrial conditions were not available so that attractive hydrolysates featuring high proportions of tripeptides could not be produced, particularly if the hydrolysate has to be obtained from a proline-rich substrate. The present invention discloses an enzyme mixture that would permit simple protocols to convert all relevant proteinaceous substrates into highly desirable hydrolysates with a good taste, an efficient gastrointestinal uptake, low allergenicity levels and, if required, a high content of bioactive peptides.).

This enzyme composition consisting of an endoprotease, preferably a proline specific endoprotease, and a tripeptidase when added to a suitable protein is able to produce the protein hydrolysate which is rich in tripeptides and optionally dipeptides whereby the di- and/or tripeptides are rich in proline at one end of the peptide.

In all applications these protein hydrolysates offer attractive advantages such as lowered allergenicities, facilitated gastrointestinal uptake, less chemical deterioration of desirable amino acids like glutamine and cystein and finally, absence of proteinaceous precipitations in acid beverages during prolonged storage periods. All these advantages can be combined if the hydrolysate is prepared using a combination of an endoprotease, preferably a proline specific endoprotease, and one or more tripeptidases. According to the invention several useful tripeptidases are preferably used in a pure or isolated state. Pure tripeptidase can be obtained for example by overexpression of the enzyme is a suitable transformed host microorganism. Preferred are those tripeptidases that exhibit a low selectivity towards the substrate to be cleaved, i.e. exhibit minimal amino acid residue cleavage preferences only. Combinations of tripeptidases that hydrolyse high percentages of the naturally occurring peptide bonds are preferred. Despite this high activity to naturally occurring peptide bonds, a total hydrolysis to free amino acids is prevented by the nature of the tripeptidases. Also tripeptidases that are optimally active between pH 4 to 8 and exhibit adequate temperature stability are preferred. Adequate temperature stability means that at least 40%, preferably at least 60%, more preferably between 70 and 100% of the initial hydrolytic activity survives after heating the enzyme together with the substrate for 1 hour at 50 degrees C. Tripeptidyl aminopeptidase is the preferred tripeptidase Tripeptidyl aminopeptidases are enzymes that can release tripeptides from the N-terminus of an oligopeptide. Little is known on enzymes that can release tripeptides from the oligopeptide's carboxyterminus ("tripeptidyl carboxypeptidases or peptidyl-tripeptidases"). The various physiological advantages of the mixture of tripeptides that can be formed by such enzymes was illustrated above. Tripeptides offer a much wider sequence variation than dipeptides can hereby increasing the chance of an optimal fit with the receptors responsible for modulating biological activities. This is well illustrated by the documented number of bioactive peptides having a carboxyterminal proline residue (see for example WO 01/68114).

Tripeptidyl aminopeptidases (EC 3.4.14) have been isolated from mammalian as well as plant sources. Microorganisms from which tripeptidylpeptidases have been isolated are for example *Streptomyces* species (JP08308565, WO 95/17512 and U.S. Pat. No. 5,856,166)), *Porphyromonas gingivalis* (WO 00/52147), *Dictyostelium discoidum* and *Aspergillus* species (WO 96/14404). To date, the occurrence of tripeptidyl carboxypeptidases (EC 3.4.15) has been demonstrated in mammalian cells and in the microorganism *Clostridium histolyticum* only.

A mixture of tripeptidases is especially preferred in the process of the present invention. We have found that such a mixture can decrease the reaction time. Moreover, a higher amount of tripeptides is formed if compared with the use of a single peptidase. peptidases especially suitable in the present invention are described in our co pending patent application PCT/EP0201984 (=WO 02/068623). These enzymes are obtained from *A. niger*, In table 1 of PCT/EP02/10984 the SEQ ID number of the tripeptidases are given. The corresponding sequences are also given in this application.

From an economic point of view the implication of our observations is that there exists a clear need in the present process for the use of tripeptidases and/or endoproteases in high quantities and in a pure or isolated form. A preferred way of obtaining purified and isolated tripeptidases is via the overproduction using recombinant DNA techniques. As many food products are acidic and long term enzyme incubations under industrial, non-sterile circumstances also require acidic incubation conditions and a processing at elevated temperatures to prevent microbial contamination, a more preferred method is the overproduction of acid stable tripeptidases exhibiting adequate stabilities under processing conditions of 50 degrees C. or higher using recombinant DNA techniques. A particularly preferred method is the overproduction of such tripeptidases derived from *Aspergillus* and a most preferred method is the overproduction of such tripeptidases from *Aspergillus niger*.

A polypeptide used in the process of the invention which has endoprotease or tripeptidase activity may be in an isolated form. As defined herein, an isolated polypeptide is an endogenously produced or a recombinant polypeptide which is essentially free from other polypeptides, and is typically at least 20% pure, preferably at least 40% pure, more preferably at least 60% pure, even more preferably at least 80% pure, still more preferably at least 90% pure, or most preferably at least 95% pure, as determined by SDS-PAGE. The polypeptide may be isolated by centrifugation, filtration (for example ultrafiltration) or chromatographic methods, or any other technique known in the art for obtaining pure proteins from crude solutions. It will be understood that the polypeptide may be mixed with carriers or diluents which do not interfere with the intended purpose of the polypeptide, and thus the polypeptide in this form will still be regarded as isolated. It will generally comprise the polypeptide in a preparation in which more than 10%, for example more than 20%, 30%, 40%, 50%, 80%, 90%, 95% or 99%, by weight of the proteins in the preparation is a polypeptide for use of the process of the present invention.

The main aim of the hydrolysates of the invention is to minimize the allergenicity or immunoresponse of the product or to facilitate gastrointestinal uptake. In the production of such hydrolysates the use of a proline specific endoprotease in combination with one or more tripeptidases is of special importance as these offer an efficient way for producing such hydrolysates.

The enzyme mixture according to the invention may comprise a tripeptidase or a mixture of tripeptidases. The enzyme mixture my also comprise a endoprotease, such as a serine protease, a metalloendoprotease, an aspartic protease, or a proline-specific endoprotease (PSE or E.C. 3.4.21.26) which work together with the tripeptidase to provide a primary protein hydrolysate. Of course the endoprotease can be one or more different endoproteases which are incubated either simultaneously or consecutively with the protein substrate, for example the proteinaceous substrate may be first digested with an endoprotease preferably a serine protease, a metalloendoprotease or an aspartic protease and subsequently, digested with a second endoprotease, preferably PSE. Before adding the second endoprotease, the enzymes already present are optionally inactivated.

Serine proteases represent a well known class of alkaline endoproteases. Examples include subtilisin (E.C. 3.4.21.62) and chymotrypsin (E.C. 3.4.21.1) which prefer cleavage of the peptide chain at the carboxy terminal side of hydrophobic amino acids such as Tyr, Trp, Phe and Leu. The enzyme mixture of the invention may contain chymotrypsin and/or subtilisin. Subtilisin is produced by species of *Bacillus*, has a particularly broad substrate specificity and a broad, alkaline pH optimum. The enzyme is optimally active between 50° C. and 60° C. The enzyme is cheaply available as a regular commercial product and is useful in the production of, for example, various milk hydrolysates. Chymotrypsin may be obtained from animal pancreas, has a somewhat narrower substrate specificity at slightly more alkaline pH values than subtilisin and is optimally active below 50 degrees C.

The class of metalloendoproteases is wide spread in bacteria, fungi and higher organisms. They can be separated into the neutral and acid metalloproteases. Of these two subclasses only the neutral proteases exhibit the desirable cleavage preference i.e. cleaving the peptide chain on the carboxy terminal side of hydrophobic amino acid residues such as Phe and Leu. Well known examples of the neutral metalloproteases are bacillolysin (E.C. 3.4.24.28) and thermolysin (E.C. 3.4.24.27) and either, or both of these, may be present in the enzyme mixture of the invention. Both enzymes are obtained from *Bacillus* species and exhibit maximum activity under neutral or slightly alkaline conditions. Less well known examples of these neutral metalloendoproteases have been obtained from *Aspergillus* species. In cases in which the proline specific endoprotease is not used for its debittering effects but to aid in the hydrolysis of proline rich protein sequences, combination with an acid metalloprotease, as for example deuterolysine (EC 3.4.24.39) can be advantageous.

Unlike the serine and metalloendopeptidases, the aspartic proteases feature an acidic pH optimum that can be advantageously used in combination with a proline-specific endoprotease and a tripeptidase that also have acidic pH optima. Among the aspartic proteases especially pepsin is recognized as an effective endoprotease with a broad specificity. Suitable *A. niger* derived aspartic endoproteases have been specified in our copending application PCT/EP02/01984.

The process according to the invention involves a combination of one or more endoproteases with one or more tripeptidases. Advantageously the enzymes are used in isolated form and in an endoprotease to tripeptidase protein ratio range between 1:0.05 and 1:50, preferably between 1:0.1 to 1:10

To establish the protein ratio of endoprotease(s) versus tripeptidase(s) as used in the process according to the invention, the substantially pure enzymes are subjected to SDS-PAGE analysis followed by a standard protein staining protocol using Coomassie Brilliant Blue. Quantification of the enzymes used is carried out using a spot densitometer measuring the integrated density values of the protein bands corresponding with the active enzymes. To prevent degradation of the enzymes during the denaturation step carried out prior to SDS-PAGE, denaturation is carried out by mixing the enzymes with a protease inhibitor, immersion of the mixture in a waterbath of 99 degrees C. for 5 minutes after which the required quantities of SOS and reducing compound are added. Serine endoproteases are inhibited by mixing with Pefabloc, metalloproteases by mixing with phosphoramidon and aspartic proteases by mixing with pepstatin. All inhibitors plus working procedures are obtainable from Roche.

Our co pending patent application PCT/EP01/14480 describes the use of a proline-specific endoprotease which, in conjunction with the prior art endoproteases, is able to generate non-bitter protein hydrolysates. This proline-specific endoprotease is an enzyme capable of cleaving peptides or polypeptides at the carboxy-terminal end of praline residues. Proline-specific endoproteases are widely found in animals and plants, but their presence in microorganisms appears to be limited. To date, proline-specific endoprotease have been identified in species of *Aspergillus* (EP 0 522 428 and WO 02/45524), *Flavobacterium* (EP 0 967 285), *Aeromonas* (J. Biochem. 113, 790-796), *Xanthomonas* and *Bacteroides*. We have shown that a high incidence of praline residues at the carboxy terminal end of peptides can be correlated with low bitterness. Moreover we have demonstrated that the desired high incidence of carboxy terminal proline residues can only be achieved with high concentrations of a proline-specific endoprotease, i.e. concentrations that exceed the activity specified in JP5015314 by several orders of magnitude and moreover in the absence of a carboxypeptidase.

In conjunction with prior art endoproteases, the proline-specific endoprotease is capable of extensively hydrolysing proline-rich proteins yielding relatively small peptides with a narrow size distribution. Because of the cleavage preference the proline-specific endoprotease, many of the peptides formed have a carboxyterminal proline residue. Furthermore, the processing of the hydrolysate is relatively simple as a debittering step by exoproteases is not involved so that only low levels of free amino acids will be formed.

From an economic point of view the implication of this observation is that there exists a clear need in the present process for the use of proline-specific endoproteases in high quantities and a pure or isolated form, which is described in our co pending application PCT/EP01/14480. A preferred way of obtaining purified and isolated PSE is via the overproduction of such a proline-specific endoprotease using recombinant DNA techniques. As many food products are acidic and long term enzyme incubations under industrial, non-sterile circumstances require acidic incubation conditions and a processing temperature of 50 degrees C. or higher to prevent microbial contamination, a more preferred method is the overproduction of an acid stable proline-specificendoprotease using recombinant DNA techniques. A particularly preferred method is the overproduction of an *Aspergillus* derived proline-specific endoprotease and a most preferred method is the overproduction of an *Aspergillus niger* derived proline-specific endopeptidase. Furthermore the enzymes according to the invention may be used in an immobilized form so that large quantities of protein containing liquids can be treated. Ways to select appropriate support materials and suitable immobilization methods have been extensively described in the literature, for example in "Immobilization of Enzymes and Cells" (ed. Gordon F. Bickerstaff; ISBN 0-89603-386-4).

Once the new enzymes have been made available in a relatively pure form, other new and surprising applications are envisaged which have technical and economical advantages.

A new application would be the creation of non-bitter hydrolysates from proteinaceous substrates with novel amino acid compositions. Such novel amino acid compositions may offer serious benefits in certain food and medical applications. Examples are casein or wheat gluten or maize protein isolate with high levels of hydrophobic amino acid residues and, more specifically, proline residues present. Hitherto such substrates were of no practical use because of the objectional bitter tastes generated upon hydrolysis and the limited degrees of hydrolysis obtained using prior art methods. Using the hydrolysis method according to the invention, new, non-bitter hydrolysates can be made available to be used in infant and clinical nutrition, in therapeutic diets as well as in consumer diets and sport nutrition.

Other benefits, not directly related to suppressing bitter tastes, include the incubation of the enzyme with food proteins to reduce their allergenicity or immunological response. Several food proteins contain highly allergenic subfractions, such as wheat gluten that contains prolamines with proline-rich peptide sequences. These proteins can be subjected to the new enzymes to alleviate their antigenicity. One specific application is the use of a combination of an endoprotease preferably a proline-specific endoprotease with a tripeptidase for oral consumption. Such a composition for oral intake could be a tablet or a pill or a powder or liquid in which the combination of the two enzymes exhibit a good shelf stability. If kept in a dry form the desired shelf stability of the enzymes will pose little technical problems. Liquid enzyme formulations providing good shelf stabilities and suitable for oral consumption have been described in the prior art. Upon oral intake and the combination of the two acid stable enzymes will aid the digestion of proline rich proteins such as caseins or glutens hereby preventing or minimising the effects described for, for example, coeliac sprue.

The proline-specific endoprotease is used to generate peptides having a carboxyterminal proline residue. Such peptides are desirable additions to various food or nutraceutical products as they have been implicated in anorectic, fibrinolytic, antithrombotic and antihypertensive effects, as well as in protection of the gastric mucosa and the prevention of rheumatoid arthritis.

In most of these new applications the proline-specific endoprotease should preferably exhibit an activity spectrum with an acidic pH optimum.

To overcome the above-mentioned problems, the invention demonstrates that the activity of an isolated, purified proline-specific endoprotease alone, i.e. without the substantial concomitant or subsequent activity of an exoproteolytic enzyme, is sufficient for significantly debittering a protein hydrolysate. Therefore the proline-specific endoprotease may comprise at least 5 units per gram protein of the enzyme preparation of the invention, preferably 10 u/g, more preferably 25 u/g and even more preferably 50 u/g. Moreover, studies conducted in accordance with the invention demonstrate that the activity of an isolated, purified proline-specific endoprotease alone, meaning without the concomitant or subsequent activity of an exoproteolytic enzyme, is sufficient to significantly decrease the overall immunogenicity level of protein hydrolysates, as well as to significantly increase their overall solubility under acidic conditions. The hydrolysates produced according to the invention are enriched in peptides having a carboxy terminal proline residue.

An embodiment of the present invention provides the use of a proline-specific endoprotease, preferably isolated and/or purified, for the high yield production of protein hydrolysates having substantially low bitterness and low allergenic properties without the concomitant production of substantial levels of free amino acids in combination with a TPAP. All the enzymes may be added at the same time to the substrate or the enzymatic process can be performed in two phases, first the PSE hydrolysis followed by the TPAP hydrolysis.

Tripeptidases are the enzymes of choice for preparing easily assimilable protein hydrolysates. Not only can the peptides formed be directly translocated over the wall of the small intestine but, due to their small size these peptides combine a good water solubility with a lack of any allergenic potential. Moreover, vulnerable but indispensible amino acids like glutamine, cysteine and tyrosine are much more stable if present in the form of tripeptides rather than free amino acids. Thus, upon digesting selected proteinaceous substrates with a suitable endoprotease in combination with a tripeptidyl peptidase, hydrolysates are formed in which selected amino acid residues are present in a stable and yet easily assimilable form. Conceivable products that can be conveniently produced using the enzyme mixture according to the invention are easily assimilable gluten hydrolysates supplying high levels of glutamine as well as hydrolysates obtained from keratin or lactalbumin-rich fractions from whey supplying high levels of cysteine. Likewise hydrolysates containing tripeptides exerting an enhanced modulating, regulatory or hormone-like activity as the result of their increased stability, for example tripeptides rich in proline or glycine residues, could be formed upon the digestion of substrates like gelatin or casein or maize protein. Because of the optimal size and enhanced stability of the peptides present in these hydrolysates, peroral uptake is likely to result in relatively high tripeptide levels in the blood circulation so that the concept of true nutraceuticals comes within reach. Enhanced effects may be attainable by minor chemical conversions of the peptides formed, e.g. cyclisation of peptides containing proline residues.

The process of the invention is suitable for preparing hydrolysates of various protein fractions. In particular, a protein substrate, such as a milk protein, may be incubated with an isolated, purified proline-specific endoprotease and a TPAP to produce a protein hydrolysate enriched in peptide fragments having a carboxy terminal proline.

The average length of the peptides in the hydrolysates is in general from 2 to 9 amino acids, preferably from 3 to 6 amino acids, more preferably from 3 to 5 amino acids. This average length is based on peptides having molecular masses from 200 to 2000 Dalton and can be calculated by taking the sum of the number of each peptide multiplied with the length of said peptide and dividing this sum by the total number of peptides.

By peptides or peptide fragments it is meant peptides with molecular masses from 200 to 2000 Dalton. These peptides can be analysed according to the LC/MC analysis as described the "Materials and Methods" section.

In general in the production of the protein hydrolysates of the invention protein substrate is substantially hydrolysed, preferably at least 20% (w/w) of the protein substrate is converted into peptides having molecular masses from 200 to 2000 Dalton. More preferably from 30 to 90% (w/w) and even more preferably from 40 to 80% (w/w) of the protein substrate is converted into such peptides.

Another embodiment of the invention is a protein hydrolysate enriched with a relatively high content of peptides having proline as the carboxy terminal amino acid residue. Since enzyme preparations typically utilized in the genesis of protein hydrolysates are not capable of generating peptides bearing proline residues at carboxy terminii, protein hydrolysates that are relatively rich in such peptides are desired.

Substrates for hydrolysis by an enzyme mixture of the invention include whole milk, skimmed milk, acid casein, rennet casein, acid whey products or cheese whey products. Industrially obtainable fractions as for example fractions enriched in lactalbumine are also useful. Quite surprisingly the *Aspergillus* derived proline specific endoprotease does not only cleave at the carboxy-terminal side of proline residues but also at the carboxy-terminal side of hydroxyproline residues which makes other, collagen based animal proteins such as gelatine as well as bones or fish-bones containing residual meat interesting substrates for the enzyme. Moreover, vegetable substrates like wheat or maize gluten and protein fractions obtained from these glutens as well as protein fractions obtained from, for example, soy, rice or corn are suitable substrates. Milk protein hydrolysates produced according to the invention may be used with or without additional filtration or purification steps in various speciality foods such as hypoallergenic hydrolysates for infant nutrition, basic hydrolysates for enteral and dietetic nutrition, as well as protein concentrates for various forms of health food. Thus, protein hydrolysates of the invention may be used to produce foodstuffs having low antigenicity, such as infant formula or requiring facilitated gastrointestinal uptake, such as various medical or health related products. In addition, enzyme preparations according to the invention may be used to reduce bitterness in foods flavored by at least one protein hydrolysate, even when the protein hydrolysate is present in large amounts. For example, foods may comprise between 5% and 10% (w/v) of a protein hydrolysate and still have their bitterness reduced using an enzyme preparation of the invention.

The present invention preferably uses an isolated or purified proline-specific endoprotease with an acidic pH optimum in a combination with one or more isolated tripeptidases exhibiting acid pH optima for the preparation of a protein hydrolysate for various food applications. Such an isolated, purified proline-specific endoprotease is defined to have at least 10 units of proline specific endoprotease activity per gram of proteinaceous material. These units should be measured using the synthetic peptide Z-Gly-Pro-pNA (Bachem, Switzerland) at 37 degrees C. and pH 7. However, if the pH optimum of the proline-specific endoprotease is below pH 6, for example in case of *Aspergillus niger* proline specific endoprotease, the units should be measured at pH 5, as specified in the Materials and Methods section. The enzyme mixture of the invention overcomes a number of disadvantages of enzyme mixtures previously known in the art. Most importantly, the isolated, purified proline-specific endoprotease is key in the production of hydrolysates which combine a low allergenic potential, a high yield and a low bitterness profile. The isolated tripeptidases are key in the generation of easily assimilable peptides without any allergenic potential and a specific, preferred amino acid composition. Moreover, the hydrolysates produced with an enzyme mixture comprising this proline-specific endoprotease are relatively stable in the body, exhibit a surprising shelf stability upon their incorporation in acid products and contain very low levels of free amino acids, such that minimal off-tastes are generated during heating steps, such as spray drying or product sterilisation. Hydrolysates according to the invention will contain less than 900 micromoles of free amino acids per gram dry weight, preferably less than 300 micromoles of free amino acids per gram dry weight more preferably less than 150 micromoles of free amino acids per gram dry weight, and even more preferably less than 50 micromoles per gram dry weight.

LEGENDS TO THE FIGURES

FIG. 1 Comparison of specificity of TPAP-A and TPAP-B using A-A-X-pNA substrates where X is all natural aminoacids, at pH 4.

FIG. 2 Composition of soluble peptides obtained by hydrolysing alfa-lactalbumin with enzyme combinations as indicated.

MATERIALS AND METHODS

Sodium caseinate containing 90% protein was obtained from DMV International (The Netherlands). Subtilisin from *B. licheniformis* (Delvolase®, 560 000 DU per gram) was obtained from DSM Food Specialities (Seclin, France).

The enzymatic activity of proline specific endoproteases exhibiting pH optima above pH 6.0 are tested according to T. Diefenthal and H. Dargatz (World Journal of Microbiology & Biotechnology 11, 209-212 (1995)) on Z-Gly-Pro-pNA 0.26 mM in phosphate buffer 0.1M pH 7.0 at 25° C. The product was monitored spectrophotometrically at 410 nm. Proline specific endoproteases from *Aspergillus* was measured according to the method described in Japanese patent JP5015314 with minor modifications. In brief the enzymatic activity is tested on Z-Gly-Pro-pNA at 37 degrees C. in a citrate/disodium phosphate buffer pH 5. pH 5.0 is chosen because in this test the pH optimum of the enzyme is below pH 6. The reaction product was also monitored spectrophotometrically at 410 nM using a molar extinction coefficient of 10500 per mol/liter. The activity of the purified tripeptidyl aminopeptidase as over produced by *A. niger* (TPAP-A) was measured in a similar way. However, in this case the synthetic substrate Ala-Ala-Phe-pNA (Bachem, Switzerland) was used in an incubation in 0.1 mol/litre citrate buffer at pH 4.0 and 60 degrees C. The purified TPAP-A had an activity of 8 units/ml.

A unit is defined as the quantity of enzyme that provokes the release of 1 μmol of p-nitroanilide per minute under these conditions.

The Degree of Hydrolysis (DH) as obtained during incubation with the various proteolytic mixtures was monitored using a rapid OPA test (JFS, Vol 66, NO 5, 2001).

Sensoric evaluation of the protein hydrolysates formed was carried out by an independent institute availing of a panel trained in detecting and ranking various levels of bitterness. During the sessions the taste trials were performed 'blind' and bitterness was scored on a scale from 0 (none)-4 (very bitter). Panel members were trained with quinine sulphate with the following solutions;
15 ppm quinine sulphate>Intensity bitter=1
20 ppm quinine sulphate>Intensity bitter=2
30 ppm quinine sulphate>Intensity bitter=3
50 ppm quinine sulphate>Intensity bitter=4

LC/MS Analysis

HPLC (high performance liquid chromatography) using a Qtof-2 (Micromass, Manchester, UK) mass spectrometer was used to separate the peptides formed during digestion with trypsin. 5 microliter of the peptide solution was trapped on a micro-precolumn, C18, 5*0.3 mm (MCA30-05-C18, LC Packings, Amsterdam, Netherlands) using Milli Q water containing 0.1% of formic acid at a flow-rate of 20 microliter/ min. The peptides were then eluted from the precolumn, using a fast gradient of 0.1% formic acid in Milli Q water (Millipore, Bedford, Mass., USA; Solution A) and 0.1% formic acid in acetonitrile (Solution B). The gradient started at 100% of Solution A and increased to 60% of solution B in 20 minutes and was kept at the latter ratio for another 5 minutes. The flow rate used during elution of the peptides was 200 nl/min. Using LC/MS/MS analysis partial amino acid sequences of the *A. niger* proline-specific endopeptidase could be determined, by de novo sequencing of suitable peptides.

HPLC using an ion trap mass spectrometer (Thermoquest®, Breda, the Netherlands) coupled to a P4000 pump (Thermoquest®, Breda, the Netherlands) was used in characterising the enzymatic protein hydrolysates produced by the inventive enzyme mixture. The peptides formed were separated using a PEPMAP C18 300A (MIC-15-03-C18-PM, LC Packings, Amsterdam, The Netherlands) column in combination with a gradient of 0.1% formic acid+1 mM nonafluoropentaoic acid (NFPA) in Milli Q water (Millipore, Bedford, Mass., USA; Solution A) and 0.1% formic acid in acetonitrile (Solution B) for elution. The gradient started at 100% of Solution A and increased to 40% of solution B in 140 minutes and was kept at the latter ratio for another 5 minutes. The injection volume used was 50 microliters, the flow rate was 50 microliter per minute and the column temperature was maintained at 30° C. The protein concentration of the injected sample was approx. 50 micrograms/milliliter.

Detailed information on the individual peptides was obtained by using the "scan dependent" MS/MS algorithm which is a characteristic algorithm for an ion trap mass spectrometer.

Full scan analysis was followed by zoom scan analysis for the determination of the charge state of the most intense ion in the full scan mass range. Subsequent MS/MS analysis of the latter ion resulted in partial peptide sequence information, which could be used for database searching using the SEQUEST application from Xcalibur Bioworks (Thermoquest®, Breda, The Netherlands). Databanks used were extracted from the OWL.fasta databank, available at the NCBI (National Centre for Biotechnology informatics), containing the proteins of interest for the application used. In those experiments in which well characterized protein substrates such as whey proteins or caseins were measured, the precision of the analysis technique was increased by omitting those MS/MS spectra with a sequence fit of less than 50%.

By using different inventive enzyme mixtures the mass range of the peptides formed starts at di- and tripeptides. By using the volatile ion-pairing reagent NFPA in combination with reversed phase liquid chromatography also smaller and more hydrophilic peptides can be monitored ending up with a mass ranging from approx. 200 to 2000 Daltons, considered suitable for further analysis by MS sequencing.

Angiotensin (M=1295.6) was used to tune for optimal sensitivity in MS mode and for optimal fragmentation in MS/MS mode, performing constant infusion of 60 mg/ml, resulting in mainly doubly and triply charged species in MS mode, and an optimal collision energy of about 35% in MS/MS mode.

LC/MS Analysis of Infant Formulae and Commercial Protein Hydrolysates.

Prior to LC/MS fatty material had to be removed from the infant formulae. To that end the complete nutrition samples (13.5 g powder in 100 ml MilliQ water) were extracted 3 times with 30 ml hexane. Small amounts of NaCl were added to improve separation of the solvent layers. Then 5 ml of the water layer was obtained and freeze dried. Prior to analysis the sample was redissolved in 25 ml of MilliQ water, centrifugated 2 times (at 13000 rpm) and filtered through a 0.22 µm filter. From pure hydrolysated samples, 400 mg was dissolved in 100 ml MilliQ water, centrifugated 2 times (at 13000 rpm) and filtered through a 0.22 µm filter. To characterise the peptides present in the commercial protein hydrolysates, the same strategy was followed as described above for the enzymatic hydrolysates formed by the inventive enzyme mixture i.e. the filtered hydrolysate was applied to the HPLC column and individual peptides with—molecular masses between 200 and 2000 daltons were further characterised by the MS/MS analysis.

Determination of the Molar Fraction of Peptides (%) Carrying a Carboxyterminal Proline.

LC/MS/MS can be used for the analysis of the C-terminus of a peptide. With an algorithm in which the peptide's molecular mass (analyzed with LC/MS) and its (partial) amino acid sequence (analyzed with LC/MS/MS) are linked with automatic search procedures within protein databanks, complex peptide mixtures can be analyzed. These options have enabled us to quantify the incidence of peptides carrying a carboxy terminal proline residue.

To determine the molar fraction of peptides carrying a carboxyterminal proline in a protein hydrolysate, individual peptide peaks eluting from the PEPMAP column are selected and partial carboxyterminal amino acid sequences are determined using the techniques specified above. Analysis of at least 20, preferably at least 30 and more preferably between 40 to 60, for example 50 of the most abundant, randomly chosen peptides thus provides insight in the frequency in which peptides carrying a proline residue at the carboxyterminus of the peptide occur. The quotient of the number of peptides found to carry a carboxyterminal proline residue times 100 and the total number of peptides analysed thus provides the molar fraction of peptides (%) carrying a carboxyterminal proline.

Determination of the Molar Fraction (%) of Proline in the Protein Substrate Used to Generate the Hydrolysate.

Any fatty material was first removed by hexane extraction as detailed in the paragraph describing LC/MS analysis of infant formulae and commercial protein hydrolysates. Acid hydrolysis of the protein substrate to convert the proteins present into free amino acids, was achieved by making a suspension of 100 milligrams of proteinaceous material in 2 milliliters 6 N HCl. Acid hydrolysis was carried out for 22 hours at 112 degrees C. in an oxygen free atmosphere. After centrifugation the supernatant was diluted 10 times in dilute HCl. After this hydrolysis the amino acids were derivatised and analysed according to the Picotag method as specified in the operators manual of the Amino Acid Analysis System of Waters (Milford Mass., USA). The level of proline present was quantitated using HPLC methods. To determine the molar fraction (%) of praline in the sample, the micromoles of proline present times 100 were divided by the sum of the micromoles of all amino acids present in the sample analysed. Since during acid hydrolysis Trp and Cys are destroyed, these two amino acids are not included in this sum of the micromoles of all amino acids.

Determination of the Free Amino Acid Levels in Protein Hydrolysates or Infant Formulae A precisely weighed sample of the proteinaceous material was dissolved in dilute acid and precipitates were removed by centrifugation in an Eppendorf centrifuge. Amino acid analysis was carried out on the clear supernatant according to the PicoTag method as specified in the operators manual of the Amino Acid Analysis System of Waters (Milford Mass., USA). To that end a suitable sample was obtained from the liquid, added to dilute acid and homogenized. From the latter solution a new sample was taken, dried and derivatised using phenylisothiocyanate. The various derivatised amino acids present were quantitated using HPLC methods and added up to calculate the total level of free amino acids in the weighed sample.

To relate this total level of free amino acids in the sample to the total level of amino acids that can be liberated from this sample, the sample is also subjected to acid hydrolysis followed by a quantification of the total free amino acids present as detailed above.

EXAMPLES

Example 1

Properties of the Tripeptidylpeptidase Encoded by Gene 12 (TPAP-A) of *Aspergillus niger*

The enzyme encoded by gene 12 (described in our copending application PCT/EP0201984) was overproduced in an *A. niger* host cell and chromatographically purified. Purification was carried out on a Resource Q column in 50 millimol/liter acetate pH 4.5. Elution by increasing the NaCl concentration yielded the enzyme in a sharp activity peak. Activity was measured by incubation with the synthetic peptide Ala-Ala-Phe-pNA. The solution with the purified enzyme contained 8 units/ml if tested on the synthetic tripeptide Ala-Ala-Phe-pNA at pH 4.0 and 60 degrees C. (see Materials & Methods section).

In a first experiment, the pure enzyme was incubated at pH 5 and 50 degrees C. with two different synthetic chromogenic substrates i.e. Ala-Ala-Phe-pNA and Ala-Phe-pNA (both from Bachem, Switserland). Stock solutions of these peptides were made in DMSO which were then diluted 100× in the desired aqueous buffer. The incubation with the Ala-Ala-Phe-pNA substrate led to a significant increase of the absorbance at 410 nm whereas the incubation with Ala-Phe-pNA did not. This observation clearly demonstrates that this tripeptidases can cleave off tripeptides only and does not exhibit aminopeptidase activity that can lead to an undesirable increase of free amino acids.

In a second experiment, the preferred stability characteristics of the enzyme encoded by gene 12 was demonstrated. Four samples of the purified enzyme were incubated at pH 5 for one hour at 0, 40, 50 and 60 degrees C. respectively. Then to each enzyme sample the above mentioned Ala-Ala-Phe-pNA substrate was added and the enzymatic activity in each heated sample was determined by measuring the increase in absorbance at 410 nm. Whereas the 0 degrees C. sample showed 100% activity, the 40 degrees sample showed 96% residual activity, the 50 degrees sample 92% residual activity and the 60 degrees sample 88% residual activity. These data confirm the surprising stability of this *Aspergillus* tripeptidase TPAP-A under processing conditions preferred by the food industry.

Finally an impression of the cleavage preferences of the current tripeptidylpeptidase was obtained. To this end an incubation was carried out with the synthetic peptides Ala-Ala Phe-pNA, Ala-Ala-Ala-pNA and Ala-Ala-Pro-pNA. The three peptides were dissolved in DMSO in 150 mM concentration. The reaction was performed in citrate buffer (0.1 M citrate) pH 4.0 and at 60° C.

To the cuvette 940 μL of buffer, 50 μL enzyme sample and 10 μL substrate were added and after stirring the reaction was measured kinetically at 405 nm for 10 min. The enzyme was tested in different dilutions.

In order to calculate the specific activity the protein concentration of the enzyme solution was determined spectrophotometrically at 280 nm using a molar extinction coefficient of 1.21 for 1 g/L (based on Trp and Tyr content in the enzyme molecule)

| substrates | dilution | U/mL | Specific activity U/mg |
|---|---|---|---|
| Ala-Ala-Phe-pNA | 1:50 | 7.81-8.95 | 2.3 |
| Ala-Ala-Ala-pNA | 1:50 to 1:200 | 76.2-81.5 | 21.8 |
| Ala-Ala-Pro-pNA | non diluted | 0.0 | 0.0 |

Upon comparison of the absorbances at 410 nm it became clear that the enzyme shows a clear preference for cleaving the Ala-Ala-Ala-pNA substrate. Ala-Ala-Phe-pNA was also cleaved but at a significant lower rate. No activity could be recorded towards the Ala-Ala-Pro-pNA substrate. The latter observation clearly demonstrates that the combination with a proline-specific endonuclease is preferred to convert protein substrates rich in proline residues into readily assimilable, degradation resistant tripeptides with carboxyterminal proline residues.

Example 2

Casein hydrolysates subjected to a proline-specific endoprotease in combination with a tripeptidylaminopeptidase are non-bitter and contain a high proportion of tripeptides having carboxyterminal proline residues.

A 6% (w/w on protein) casein solution was prepared by dissolving sodium caseinate in water. After adjustment of the pH to 8.0 by NaOH, the serine protease Delvolase was added to a concentration of 4% (volume of the commercial enzyme product per weight of sodium caseinate) and the mixture was incubated for 2.5 hours at 60 degrees C. under non-pH-stat conditions. Then the reaction was stopped by lowering the pH to 5.0 using lactic acid followed by a heat treatment of 10 minutes at 90 degrees C. The solution was cooled down to 50 degrees C. and two samples were taken. The first sample (Sample A) served as a reference characterizing the material that has been subjected to the action of a broad spectrum serine protease only. The second sample was used for subsequent incubations with EndoPro ("EndoPro" refers to an overproduced and chromatographically purified proline specific endoprotease from *A. niger* as described in WO 02/45524) and finally TPAP-A. The incubation with EndoPro was carried out by adding a chromatographically purified solution of the overproduced proline specific endoprotease from *A. niger* in a concentration of 2 units/gram protein (see our copending application PCT/EP01 (14480=WO02/45524). After incubating for 16 hours at 50 degrees C. under non-pH-stat conditions the EndoPro enzyme was inactivated by another heat treatment to yield Sample B.

In this stage Samples A and B were sensorically evaluated by a trained panel. The two samples were tasted "blind" and then scored on a scale from 0 (non bitter) to 4 (very bitter) as described in the Materials & Methods section. Sample A was unanimously scored as "very bitter", Sample B was unanimously scored as "non bitter". This outcome confirmed the surprising debittering capacity of the EndoPro enzyme once more.

Part of Sample B was then incubated with 20 units of chromatographically purified TPAP-A per gram of casein protein during 5 hours at pH 4.0 and 60 degrees C. Like before the enzyme reaction was terminated by heating of the solution for 10 minutes at 95 degrees C. to yield Sample C.

Samples A, B and C were then subjected to LC/MS analysis (see Materials & Methods section) to determine the size distribution of major peptides present. From all hydrolysates at least 124 different peptides were analysed. The data obtained are shown underneath.

| Enzymes used to prepare casein hydrolysate | Heptapeptides or smaller (molar % of all peptides detected) | Di + tripeptides (molar % of all peptides detected) | Tripeptides having carboxyterminal proline residues (molar % of all tripeptides detected) |
|---|---|---|---|
| Subtilisin ("Delvolase") | 68 | 15 | 0 |
| +EndoPro (PCT/EP02/01984) | 65 | 17 | 26 |
| +EndoPro + TPAP-A (Example 1) | 76 | 21 | 38 |

Combining the results of the sensory evaluation and the LC/MS analysis, it is clear that an incubation with both EndoPro and TPAP-A (i.e. after an incubation with subtilisin) yields a superior product in terms of bitterness (a casein hydrolysate shows no bitterness after incubation with EndoPro), allergenicity (peptides smaller than 8 amino acid residues) and content of potentially bioactive peptides (tripeptides resisting proteolytic degradation because of their carboxyterminal proline residue).

Example 3

Frequency of Di- and Tripeptides Having Carboxyterminal Proline Residues in a Commercial Casein Based Infant Formula Product Among the various infant formula products tested (see Example 6 in our copending application PCT/EP01/14480) Nutramigen (Mead Johnson, containing 14 grams of casein hydrolysate per 100 gram powder) contains the highest (i.e. 22%) molar fraction of peptides carrying C-terminal proline. In the present Example we show the results of a LC/MS analysis of this hydrolysate with a focus on its content in di and tripeptides and the frequency of such peptides having carboxyterminal proline residues.

Prior to LC/MS analysis the fatty material present in infant formulae had to be removed. As specified in the Materials & Methods section this was carried out by a hexane extraction. The aqueous phase thus obtained was centrifuged, filtered and then subjected to LC/MS analysis to characterize the various peptides present.

According to the results obtained, the molar fraction of casein derived di- to heptapeptides as present in Nutramigen accounts for 83% of all peptides detected. Furthermore the molar fraction of di- and tripeptides as present amongst all peptides detected in Nutramigen could be shown to amount to 18%. Among the tripeptides identified, a molar fraction of 23% could be shown to have a carboxyterminal proline residue.

Despite the fact that the protein hydrolysate used represents a product which has probably been highly purified and selectively enriched by a number of techniques such as ultrafiltration and chromatography, the hydrolysate exhibits a low level of carboxyterminal proline residues which implies considerable bitterness and a limited fraction of protease resistant tripeptides only.

Example 4

Beta-Casein Hydrolysates Obtained by a Proline-Specific Endoprotease in Combination with a Tripeptidyl Aminopeptidase Contain High Proportions of Tripeptides as Well as Peptides Having Carboxyterminal Proline Residues To allow a more precise LC/MS/MS analysis of the various reaction products obtained by combining a proline-specific endoprotease with a tripeptidylpeptidase, another hydrolysis experiment was carried out in which pure bovine beta casein was used as the substrate. To that end a 0.2% (w/w on protein) solution was prepared by dissolving pure beta-casein (Sigma) in water and adjusting the pH to 8.0 by NaOH. Then the serine protease subtilisin (Delvolase) was added to a concentration of 5% (volume of the commercial enzyme product per weight of beta-casein) and the mixture was incubated for 1 hour at 60 degrees C. under non-pH-stat conditions. The reaction was stopped by lowering the pH to 5.5 using lactic acid followed by a heat treatment of 10 minutes at 90 degrees C. Then the mixture was cooled down to 50 degrees C. and a sample was taken for LC/MS/MS analysis. A subsequent incubation with EndoPro (see Example 2) was carried out by adding a chromatographically purified solution of the overproduced proline specific endoprotease from *A. niger* in a concentration of 20 units/gram protein. After incubating for 2 hours at 50 degrees C. under non-pH-stat conditions the EndoPro enzyme was inactivated by another heat treatment to yield another sample for LC/MS/MS analysis. Finally chromatographically purified TPAP-A (see Example 1) was added in a concentration of 4 units per gram substrate and the incubation was continued for 2 hours at 60 degrees C. and then inactivated by heating to yield another LC/MS/MS sample. Subsequent incubations were carried out on beta-casein without Delvolase using EndoPro and TPAP, either alone or in combination, under the above described conditions. The latter samples were also subjected to LC/MS/MS analysis. The data obtained are shown underneath.

| Enzymes used to prepare beta-casein hydrolysate | Number of peptides analysed | Peptides with C-terminal-Pro (molar % of all peptides analysed) | Di + tripeptides (molar % of all peptides analysed) | Tripeptides (molar % of all tripeptides analysed) |
|---|---|---|---|---|
| Subtilisin | 93 | 0 | 12 | 6 |
| Subtilisin + EndoPro | 68 | 41 | 34 | 25 |

-continued

| Enzymes used to prepare beta-casein hydrolysate | Number of peptides analysed | Peptides with C-terminal-Pro (molar % of all peptides analysed) | Di + tripeptides (molar % of all peptides analysed) | Tripeptides (molar % of all tripeptides analysed) |
| --- | --- | --- | --- | --- |
| Subtilisin + EndoPro+TPAP-A | 69 | 36 | 45 | 36 |
| EndoPro | 55 | 49 | 11 | 11 |
| TPAP-A | 1 | 0 | 100 | 100 |
| EndoPro + TPAP-A | 68 | 40 | 43 | 40 |

Despite the broad specificity of the TPAP-A enzyme used (see Example 5), incubating the pure beta-casein with just the TPAP-A enzyme results in the release of a single peptide only, i.e. the N-terminal tripeptide Arg-Glu-Leu of beta-casein. For an unknown reason the TPAP-A enzyme used cannot remove the next tripeptide from this substrate hereby clearly demonstrating the need for combining the TPAP with an endoprotease such as subtilisin or EndoPro. The results shown above clearly indicate that such combinations of a TPAP with an endoprotease lead to a considerable increase in the number of tripeptides generated. Combinations involving EndoPro all show an impressive increase in the number of peptides having carboxyterminal proline residues.

Example 5

Different Tripeptidases have Different Substrate Specificities

Different tripeptidases may possess different substrate specificities so that combinations of a proline-specific endoprotease with different tripeptidases will lead to protein hydrolysates with different tripeptide compositions. To illustrate this, a complete set of chromogenic peptide substrates (Ala-Ala-X-pNA, X representing the various natural amino acid residues) was obtained from Pepscan (Lelystad, The Netherlands) after which the amino acid preferences of not only TPAP-A (corresponding with the enzyme encoded by gene 12 as described in our copending application PCT/EP02/01984 and overproduced in an *A. niger* host cell) was characterized but also of tripeptidylaminopeptidase TPAP-B (corresponding with the enzyme encoded by gene 10 as described in our copending application PCT/EP02/01984 and overproduced in an *A. niger* host cell). Just as enzyme TPAP-A, the overproduced and secreted enzyme TPAP-B was first chromatogaphically purified; in this case on a Q sepharose FF column (AA1188, Pharmacia) equilibrated in 20 millimol/l Bis Tris buffer, pH 5.5 and eluted with a gradient containing 1 mol/l NaCl in the same buffer.

Preincubation of enzymes TPAP-A and TPAP-B with a subset of the synthetic peptides indicated that both tripeptidases have their optimum between pH 3 and 5. Therefore, incubation with the complete set of chromogenic substrates to determine the cleavage preference of the two enzymes was done at pH 4.0. Stock solutions of the various synthetic substrates were prepared in DMSO in a concentration of 150 millimol/l. These stock solutions were then diluted 100 times in 0.1 mol/l sodium acetate, 20 millimol/l CaCl2 pH 4.0 after which 200 microliter of each solution was transferred to individual microtiter plate wells. After equilibration at 40 degrees C., the reaction was started by adding 200 microliter of the chromatographically purified tripeptidase to each well. Extinction development was followed at 405 nm using a Tecan Genios micro titre plate reader. Efficiencies of both enzymes towards the various substrates are presented underneath in which the activity towards the Ala-Ala-Ala-pNA substrate was used as the 100% value. The various letters on the X-axis in the figure underneath refer to the international one letter symbols used to specify the amino acid residue "X" in the Ala-Ala-X-pNA substrate, The data obtained clearly illustrate (see FIG. 1) the different substrate specificities of the TPAP-A and the TPAP-B enzyme. Whereas both enzymes exhibit a preference for cleaving at the C-terminus of amino acids like Asp ("D"), Glu ("E") and Gln ("Q"), enzymeTPAP-B is more efficient towards the amino acid residues Tyr ("Y"), Trp ("W"), Thr ("T") and Ser ("S").

Example 6

Benefits of Combining a Proline-Specific Endoprotease with a Tripeptidylaminopeptidase on Substrates Low in Proline The benefits of hydrolysing proline-rich protein substrates such as caseins or glutens or collagen-based compounds with the combination of a proline-specific endoprotease and a tripeptidylpeptidase has been adequately demonstrated in the previous Examples. Here we demonstrate that the enzyme combination is also beneficially used in the hydrolysis of substrates with lower proline contents.

A crude lactalbumin fraction from bovine milk (Sigma) was suspended in water in a concentration of 20 grams/liter after which the pH was adjusted to 8.0. The serine protease subtilisin (Delvolase) was added to a concentration of 4% (volume of the commercial enzyme product per weight of the substrate) and the mixture was incubated for 2 hours at 60 degrees C. under non-pH-stat conditions. Then the pH of the suspension was lowered to pH to 4.5 using citric acid and divided into 4 portions. One portion was heated to inactivate the Delvolase enzyme and then kept frozen until LC/MS/MS analysis. To the other three portions either chromatographically purified Endopro enzyme was added (1 unit/gram lactalbumin) or tripeptidylaminopeptidase (TPAP-A; 20 units/gram of lactalbumin) or a combination of EndoPro and TPAP-A (1 unit+20 units/gram lactalbumin; see Materials&Methods for unit definitions). The mixtures were incubated overnight at 50 degrees C., subjected to a heat treatment to inactivate the enzymes and stored at −20 degrees C. Samples were first centrifuged and the clear supernatant was used for LC/MS/MS analysis. Only those peptides fitting with the amino acid sequence of alfa-lactalbumin were taken into account.

The LC/MS/MS data obtained are shown in FIG. 2 peptide length in amino acid residues is depicted on the X-axis and on the Y-axis the number of peptides analysed. Even without a recalculation of peptides of a specific length into percentages of the total peptides analysed, the benefits of an incubation with either an proline-specific endopeptidase or a tripeptidase or a combination of these two enzymes, become visible. Together with the results provided in the previous Examples the data obtained clearly demonstrate that the combination of a proline-specific endoprotease with a tripeptidase provides superior hydrolysates, be it on proline-rich or on other proteinaceous substrates.

We claim:

1. A method of producing a protein hydrolysate comprising tripeptides having a formula $Xaa_1$-$Xaa_2$-Pro wherein $Xaa_1$ is a naturally occurring amino acid other than Pro and $Xaa_2$ is a naturally occurring amino acid, comprising contacting a protein substrate with a proline-specific endoprotease and a tripeptidase, said proline-specific endoprotease producing peptides carboxyterminated with proline.

2. The method of claim 1 wherein at least 20 molar % of peptides in said protein hydrolysate having a molecular weight of 200 to 2000 Da is present in the protein hydrolysate as tripeptides.

3. The method of claim 1 wherein at least 20% of the proline present in a starting protein that forms the protein hydrolysate is present in the tripeptides.

4. The method of claim 1 wherein at least 30% of the tripeptides have a carboxy terminal proline.

5. The method of claim 1 wherein at least 70 molar % of peptides present in the hydrolysate contain 2 to 7 amino acid residues (dipeptide to heptapeptide).

6. The method of claim 1 wherein the protein substrate is first contacted with a serine protease, aspartic protease or metalloendoprotease and subsequently the tripeptidase.

* * * * *